United States Patent
Danilov et al.

(10) Patent No.: US 10,293,163 B1
(45) Date of Patent: *May 21, 2019

(54) NON-INVASIVE NEUROMODULATION (NINM) FOR REHABILITATION OF BRAIN FUNCTION

(71) Applicants: Yuri P. Danilov, Middleton, WI (US); Mitchell E. Tyler, Madison, WI (US); Kurt A. Kaczmarek, Madison, WI (US)

(72) Inventors: Yuri P. Danilov, Middleton, WI (US); Mitchell E. Tyler, Madison, WI (US); Kurt A. Kaczmarek, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/283,894

(22) Filed: Oct. 3, 2016

Related U.S. Application Data

(63) Continuation of application No. 15/207,029, filed on Jul. 11, 2016, now Pat. No. 9,656,069, which is a continuation of application No. 14/815,171, filed on Jul. 31, 2015, now Pat. No. 9,597,504, which is a continuation of application No. 14/689,462, filed on Apr. 17, 2015, now Pat. No. 9,597,501, which is a continuation of application No. 14/341,141, filed on Jul. 25, 2014, now Pat. No. 9,020,612, which is a continuation of application No. 14/340,144, filed on Jul. 24, 2014, now Pat. No. 8,909,345, which is a
(Continued)

(51) Int. Cl.
*A61N 1/18* (2006.01)
*A61N 1/36* (2006.01)
*A61N 1/05* (2006.01)

(52) U.S. Cl.
CPC ....... *A61N 1/36103* (2013.01); *A61N 1/0548* (2013.01); *A61N 1/36082* (2013.01)

(58) Field of Classification Search
CPC .. A61H 21/00; A61N 1/36103; A61N 1/0526; A61N 1/0548; A61N 1/0492
See application file for complete search history.

(56) References Cited

U.S. PATENT DOCUMENTS 2,055,540 A    9/1936   Karnofsky
3,851,651 A    12/1974  Icenbice, Jr.
(Continued)

FOREIGN PATENT DOCUMENTS

EP      2671612 A1       2/2013
KR     20110038314 A     4/2011
(Continued)

*Primary Examiner* — Alyssa M Alter
(74) *Attorney, Agent, or Firm* — Proskauer Rose LLP

(57) ABSTRACT

A method to provide non-invasive neurostimulation to enhance a subject's proficiency in an exercise includes: (a) engaging a subject in a physical or mental exercise, the subject having no cognitive, physical or emotional impairment; (b) providing intraoral cutaneous stimulation of at least one of the subject's trigeminal nerve, facial nerve or hypoglossal nerve by delivering electrical pulses to one or more stimulators situated within the subject's mouth, the delivery of electrical pulses being (i) contemporaneously with and independent of the subject's engagement in the exercise, and (ii) independent of the subject's surrounding environment; and (c) repeating steps (a) and (b) on a periodic basis.

19 Claims, 3 Drawing Sheets

Related U.S. Application Data continuation of application No. 12/348,301, filed on Jan. 4, 2009, now Pat. No. 8,849,407.

(60) Provisional application No. 61/019,061, filed on Jan. 4, 2008, provisional application No. 61/020,265, filed on Jan. 10, 2008.

(56) References Cited

U.S. PATENT DOCUMENTS

| | | |
|---|---|---|
| 4,865,048 A | 9/1989 | Eckerson |
| 4,924,880 A | 5/1990 | O'Neill et al. |
| 4,995,404 A | 2/1991 | Nemir |
| 5,259,762 A | 11/1993 | Farrell |
| 5,265,624 A | 11/1993 | Bowman |
| 5,269,303 A | 12/1993 | Wernicke et al. |
| 5,299,569 A | 4/1994 | Wernicke et al. |
| 5,540,734 A * | 7/1996 | Zabara ............... A61N 1/36082 600/26 |
| 5,553,626 A | 9/1996 | Burger et al. |
| 5,792,067 A | 8/1998 | Karell |
| 5,794,621 A | 8/1998 | Hogan et al. |
| 5,878,154 A | 3/1999 | Schimmelpfennig |
| 6,066,163 A | 5/2000 | John |
| 6,089,864 A | 7/2000 | Buckner et al. |
| 6,161,044 A | 12/2000 | Silverstone |
| 6,169,781 B1 | 1/2001 | Doebert |
| 6,267,733 B1 | 7/2001 | Peterson et al. |
| 6,326,901 B1 | 12/2001 | Gonzales |
| 6,339,725 B1 | 1/2002 | Naritoku et al. |
| 6,366,813 B1 | 4/2002 | DiLorenzo |
| 6,366,814 B1 | 4/2002 | Boveja et al. |
| 6,405,079 B1 | 6/2002 | Ansarinia |
| 6,430,450 B1 | 8/2002 | Bach-y-Rita et al. |
| 6,463,328 B1 | 10/2002 | John |
| 6,526,318 B1 | 2/2003 | Ansarinia |
| 6,546,291 B2 | 4/2003 | Merfeld et al. |
| 6,556,868 B2 | 4/2003 | Naritoku et al. |
| 6,954,668 B1 | 10/2005 | Cuozzo |
| 7,228,178 B2 | 6/2007 | Carroll et al. |
| 7,236,830 B2 | 6/2007 | Gliner |
| 7,333,020 B2 | 2/2008 | Cohen et al. |
| 7,483,747 B2 | 1/2009 | Gliner et al. |
| 7,563,929 B2 | 7/2009 | Hobbs et al. |
| 7,565,200 B2 | 7/2009 | Wyler et al. |
| 7,640,062 B2 | 12/2009 | Shalev |
| 7,672,730 B2 | 3/2010 | Firlik et al. |
| 7,725,192 B2 | 5/2010 | Eskandar et al. |
| 7,747,325 B2 | 6/2010 | Dilorenzo |
| 7,768,499 B2 | 8/2010 | Sturtz |
| 8,290,582 B2 | 10/2012 | Lin et al. |
| 9,656,069 B1 * | 5/2017 | Danilov ............. A61N 1/36014 |
| 2003/0220677 A1 | 11/2003 | Doan et al. |
| 2004/0073270 A1 | 4/2004 | Firlik et al. |
| 2004/0073271 A1 * | 4/2004 | Harry ................ A61N 1/0452 607/48 |
| 2005/0089829 A1 | 4/2005 | Wasowicz |
| 2005/0197529 A1 | 9/2005 | Hoshihara et al. |
| 2005/0203582 A1 | 9/2005 | Healy et al. |
| 2005/0240253 A1 | 10/2005 | Tyler et al. |
| 2006/0161218 A1 | 7/2006 | Danilov |
| 2006/0241718 A1 | 10/2006 | Tyler et al. |
| 2007/0248238 A1 | 10/2007 | Abreu |
| 2007/0250119 A1 | 10/2007 | Tyler et al. |
| 2007/0293917 A1 | 12/2007 | Thompson et al. |
| 2007/0293918 A1 | 12/2007 | Thompson et al. |
| 2008/0009772 A1 | 1/2008 | Tyler et al. |
| 2008/0027510 A1 | 1/2008 | McClure et al. |
| 2008/0082131 A1 | 4/2008 | Llanos |
| 2008/0208287 A1 | 8/2008 | Palermo et al. |
| 2008/0222670 A1 | 9/2008 | Lee et al. |
| 2008/0228239 A1 | 9/2008 | Tyler et al. |
| 2008/0233541 A1 | 9/2008 | De Vreese et al. |
| 2008/0234604 A1 | 9/2008 | Burgmans |
| 2008/0281550 A1 | 11/2008 | Hogle et al. |
| 2009/0048647 A1 | 2/2009 | Tingey |
| 2009/0082831 A1 | 3/2009 | Paul et al. |
| 2009/0082839 A1 | 3/2009 | Lindquist et al. |
| 2009/0306741 A1 | 12/2009 | Hogle et al. |
| 2009/0312808 A1 | 12/2009 | Tyler et al. |
| 2009/0312817 A1 | 12/2009 | Hogle et al. |
| 2009/0326604 A1 | 12/2009 | Tyler et al. |

FOREIGN PATENT DOCUMENTS

| | | |
|---|---|---|
| RU | 2215558 C2 | 11/2003 |
| RU | 2215558 C2 | 11/2003 |
| RU | 2248227 C1 | 3/2005 |
| SU | 1068128 A1 | 1/1984 |
| WO | 02066111 A1 | 8/2002 |

* cited by examiner

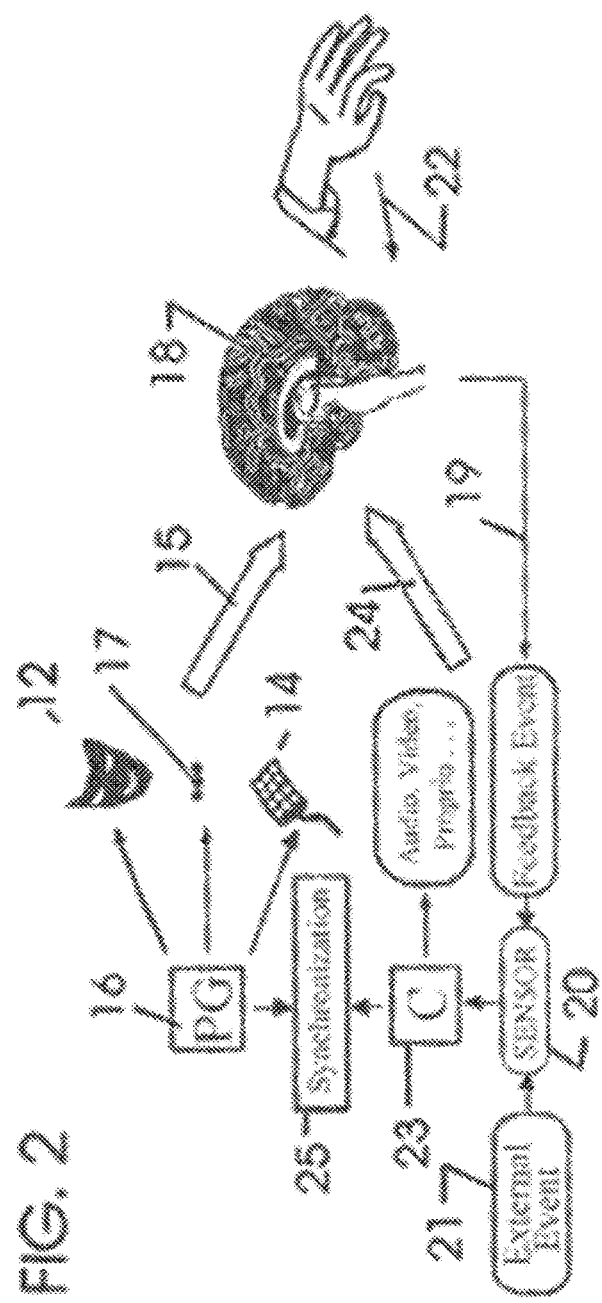

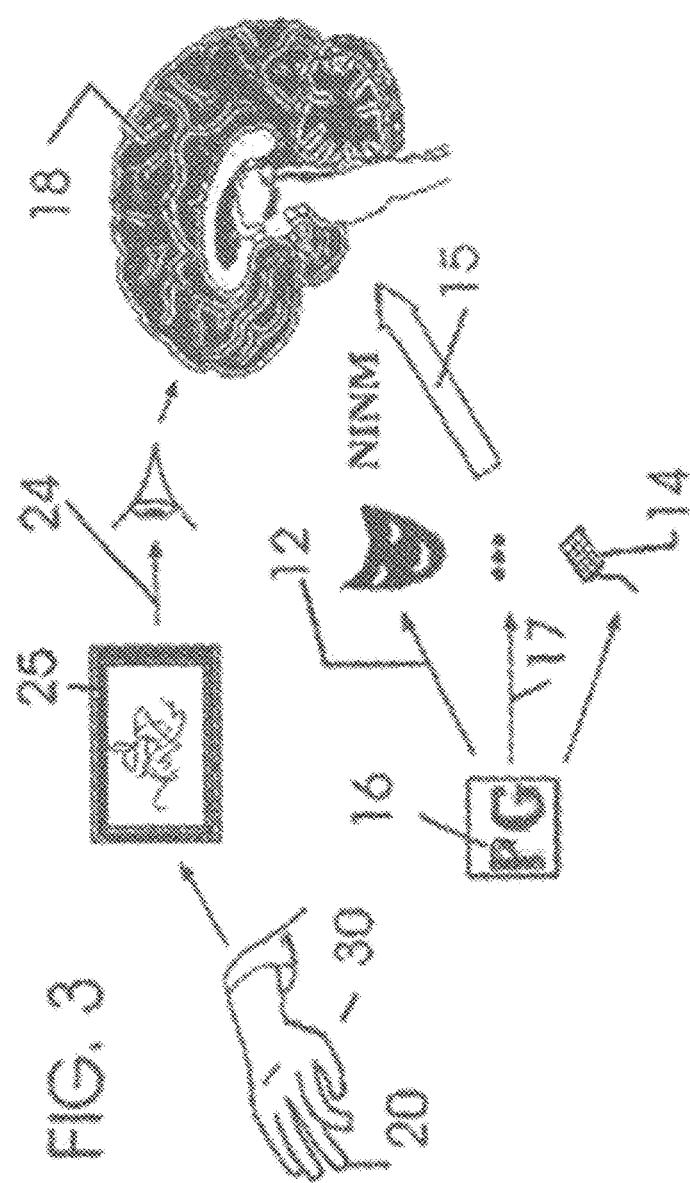

NON-INVASIVE NEUROMODULATION (NINM) FOR REHABILITATION OF BRAIN FUNCTION

CROSS-REFERENCE TO RELATED APPLICATIONS

This application is a continuation of, claims priority to and the benefit of, and incorporates by reference herein in its entirety, U.S. patent application Ser. No. 15/207,029 filed Jul. 11, 2016, and issued as U.S. Pat. No. 9,656,069 on May 23, 2017, which is a continuation of U.S. patent application Ser. No. 14/815,171 filed Jul. 31, 2015, and issued as U.S. Pat. No. 9,597,504 on Mar. 21, 2017, which is a continuation of U.S. patent application Ser. No. 14/689,462, filed Apr. 17, 2015, and issued as U.S. Pat. No. 9,597,501 on Mar. 21, 2017, which is a continuation of U.S. patent application Ser. No. 14/341,141, filed Jul. 25, 2014 and issued as U.S. Pat. No. 9,020,612 on Apr. 28, 2015, which is a continuation of U.S. patent application Ser. No. 14/340,144, filed Jul. 24, 2014, and issued as U.S. Pat. No. 8,909,345 on Dec. 9, 2014, which is a continuation of U.S. patent application Ser. No. 12/348,301, filed Jan. 4, 2009, and issued as U.S. Pat. No. 8,849,407 on Sep. 30, 2014, which claims the benefit of and priority to U.S. Provisional Application No. 61/019,061 filed Jan. 4, 2008 and U.S. Provisional Application No. 61/020,265 filed Jan. 10, 2008, the entireties of which are incorporated by reference herein.

STATEMENT OF GOVERNMENT INTEREST

This invention was made with government support under grant NS048903 awarded by the National Institutes of Health. The government has certain rights in the invention.

FIELD OF THE INVENTION

This document concerns an invention relating generally to treatment of neurological impairments, and more specifically to methods and devices for enhancing neurorehabilitation.

BACKGROUND OF THE INVENTION

Neurorehabilitation is an emerging field in medical science wherein patients suffering from damage to, or impairment of, all or a portion of their central nervous system (CNS) are treated to rehabilitate neural pathways, and/or establish new neural pathways, to at least partially compensate for the damage/impairment. Neurorehabilitation is therefore somewhat different from neural substitution, where devices are used to try to provide new neural inputs which serve as a proxies for impaired neural inputs—for example, devices which collect images of a patient's surroundings and then provide tactile feedback to the patient in dependence on the collected images, such that the patient is given tactile input as a substitute for visual input. Examples of neural substitution devices are described in prior patent applications which name the inventors of the present invention, e.g., US Published Patent Applns. 20050240253, US20060161218, 20060241718, 20070250119, 20080009772, and 20080228239 (all of which are incorporated by reference herein).

At the time this document was prepared, neurorehabilitation was commonly effected by non-invasive methods such as physical therapy, occupational therapy, or speech therapy, which basically involves the use of exercise to attempt to increase a patient's abilities. For example, one suffering from a spinal cord injury might exercise an affected area of the body to increase coordination and range of motion. These methods suffer from the disadvantage of being time-consuming, difficult and exhausting for the patient. Invasive methods also exist, such as electrostimulation, wherein electrodes are implanted to deliver electricity at or near neural pathways to enhance neural function, and/or to counter "erroneous" neural function. For example, deep brain stimulation (DBS) may be used for treatment of Parkinson's Disease and depression, left vagal nerve stimulation (LVNS) may be used for treatment of epilepsy, or sub-dural implantable stimulators may be used to assist with stroke recovery. These invasive methods are risky, still largely experimental, and expensive, and thus are generally used as a last resort when all other therapeutic interventions have failed. Additionally, they have not yet proven to be generally usable with other severe CNS disorders such as traumatic brain injury, stroke, or a sensory-motor polytrauma experienced by wounded military personnel, for example. It would therefore be useful to have additional methods and devices available for neurorehabilitation which are noninvasive or minimally invasive, inexpensive, and which eliminate or reduce the need for the ordeal of physical therapy and similar noninvasive methods.

SUMMARY OF THE INVENTION

The invention, which is defined by the claims set forth at the end of this document, is directed to methods—generally referred to herein as "non-invasive neuromodulation" or NINM—and NINM devices which at least partially alleviate the aforementioned problems. A basic understanding of some of the features of preferred versions of the invention can be attained from a review of the following brief summary of the invention, with more details being provided elsewhere in this document.

It has been found that neurorehabilitation can be assisted in a patient by having the patient engage in a task wherein the patient's ability to perform the task is hindered by impairment of the user's nervous system, and at the same time stimulating the patient's head and/or neck (or more specifically, providing stimulation detectable by one or more branches of the trigeminal nerve). For example, stimulation might be provided to the patient's face, tongue, forehead, ears, scalp, or neck while the patient attempts to maintain a normal posture, in the event of a patient with vestibular dysfunction (i.e., having difficulties with balance owing to impairment of the vestibular system); or while the patient moves his/her limb(s), in the case of apraxia (i.e., impairment of the ability to make purposeful/planned movement); or while the patient undergoes speech exercises, in the case of dysarthria (i.e., impaired speaking). It has been found that such stimulation can expedite neurorehabilitation, with the patient's ability to successfully perform the task being enhanced for at least some period of time after the stimulation ceases. Thus, for example, it has been found that where patients with vestibular dysfunction are subjected to stimulation while practicing posture/gait exercises, and they then cease the exercises and stimulation, their vestibular function is improved for at least a period of time thereafter, and for a longer period of time than if the stimulation was not provided. Thus, the foregoing methodology can be used to enhance the efficacy of conventional therapy.

The stimulation is preferably provided to the patient cutaneously (i.e., upon the patient's skin) so that it is noninvasive, though subcutaneous stimulation is also possible. The stimulation is preferably delivered by the use of stimulators, e.g., electrical elements (e.g., electrodes) for delivery of electrical stimulation, mechanical/electromechanical actuators (preferably piezo actuators, shape metal alloy actuators, MEMS actuators, or other compact devices), thermal elements (e.g., resistance heating elements or Peltier/Seebeck/Thomson elements), and/or electromagnetic elements (i.e., elements for emitting electromagnetic energy in the visible or invisible spectrum, e.g., radio wave emitters, microwave emitters, infrared emitters, ultraviolet emitters, etc.). In all cases, stimulation is delivered at intensities such that it is detectable by the patient's nerves, but at the same time such that tissue damage is avoided. Electrodes have been found to work well in practice, and are particularly preferred types of stimulators. These stimulators might be arrayed across all or a portion of one or more of a mask, a collar, a mouthpiece, or the like. As examples of masks, these could be provided in the form of a domino mask, ski mask, or other common mask; in the form of pads/patches covering all or some of the cheeks, chin, upper lip, nose, forehead, or other portions of the head and/or neck; or in the form of a cap/helmet masking portions of the head away from the face and neck (and perhaps masking portions of the face and/or neck as well). Collars could take the form of (for example) sleeves/bands covering some or all of the neck, and/or some or all of the forehead, or a portion of the face. As examples of mouthpieces, these might be provided in the form of a retainer, a mouthguard, or the like. Thus, such a device might simply be put on by a patient for wear during exercises, without the need for intrusive measures or other burdensome or painful procedures.

Stimulation is preferably generated by a pattern generator which delivers stimulation (e.g., electrical pulses) in a random pattern, or in a repeating pattern such as brief pulses provided at a regular frequency. It is notable that the stimulation pattern need not, and preferably does not, rely on any feedback from the patient and/or the patient's surroundings—for example, the stimulation pattern need not be varied if the patient is monitored and it is determined that the patient is having difficulty with the task (or conversely if the patient is performing the task well). Thus, the pattern generator can simply be set to a random or predetermined pattern by a therapist or by the patient, and the stimulators can continue to deliver this same preset pattern as the patient performs the task (and for any post-task stimulation period thereafter). The pulses are preferably delivered to the patient above the patient's threshold of sensory perception (i.e., such that the patient can feel them), but below the level of discomfort. However, it is believed that the invention may also yield results if the pulses are delivered to the patient just below the patient's threshold of perception (i.e., such that the patient does not notice them, at least unless the patient concentrates on feeling them).

It has been found that improvement in patients' abilities seems to be best effected if the following methodology is followed. Initially, while stimulation is supplied to the patient, the patient is made to perform the difficult task (one hindered by neural impairment) at low intensity. This is believed to provide the patient with confidence and proficiency, and can be performed for a short time period (e.g., for 5 minutes). The patient is then made to perform the task at high intensity, preferably at the limit of their ability, in conjunction with stimulation. Assistance can be provided if needed, and this step can also be performed for a short time period (e.g., for 5 minutes). The patient then performs the task at moderate intensity in conjunction with stimulation, again for a short time period (e.g., for 5 minutes). Finally, after a short rest, the patient might undergo a period of stimulation (e.g., for 20 minutes) during which the task is again performed at moderate intensity. This routine is preferably performed twice per day, with a span of about four hours separating the sessions. It is also notable that the invention also appears to improve cognition and mood in at least some cases, i.e., the invention may also be useful for treatment of conditions such as learning, attention, and/or memory disorders (e.g., Alzheimer's disease, attention deficit disorder, etc.), as well as mood disorders (e.g., depression, post-traumatic stress disorder, obsessive-compulsive disorder, etc.).

Further advantages, features, and objects of the invention will be apparent from the remainder of this document in conjunction with the associated drawings.

BRIEF DESCRIPTION OF THE DRAWINGS

FIG. 2 is a simplified signal flow chart similar to that of FIG. 1 in which the stimulation is synchronized with an activity and/or external stimuli related to the neural impairment;

FIG. 3 is a simplified signal flow chart similar to that of FIG. 1 wherein the stimulation is simply contemporaneous with an activity associated with the neural impairment.

DETAILED DESCRIPTION OF PREFERRED VERSIONS OF THE INVENTION

Figure 1:
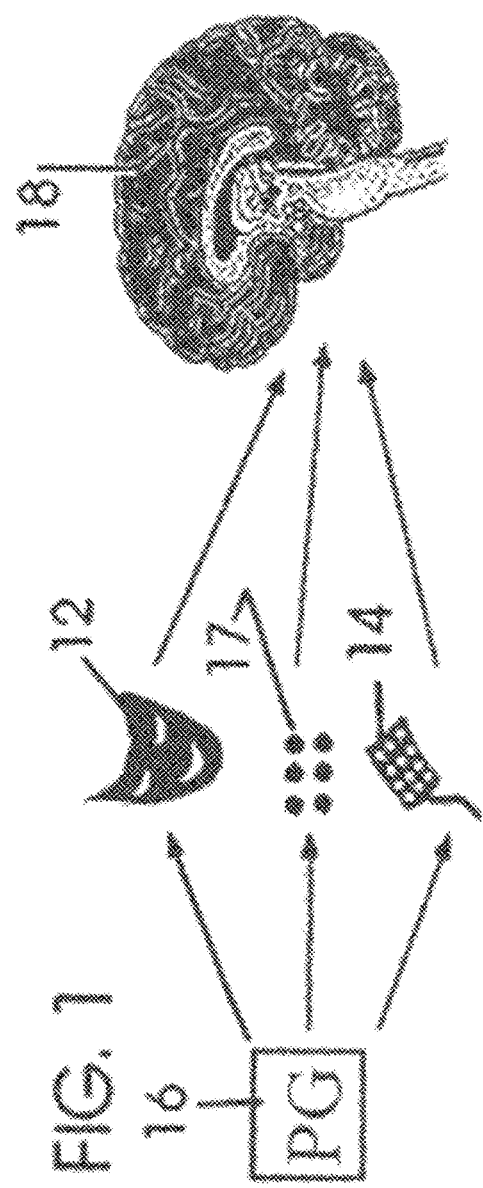
FIG. 1 is a simplified signal flow chart of an exemplary version of the invention wherein stimulation is applied to a patient independently of any activity associated with a brain dysfunction or other neural impairment.

To expand on the discussion above, FIG. 1 illustrates an exemplary version of the invention wherein a facial mask 12 or tongue plate 14 bears a set of spatially arrayed electrical, mechanical, thermal, electromagnetic, or other stimulators 17, such as electrodes. These stimulators 17 preferably provide stimulation to the trigeminal nerve or subportions thereof, e.g., to the lingual nerve, and thereby stimulate the brain. Such stimulation is preferably non-invasive, that is, in distinction from brain-penetrating electrodes or other matter which penetrates or otherwise modifies the flesh, and is most preferably cutaneous (i.e., effected by stimulators 17 which simply rest in contact with the skin).

The facial mask 12 or tongue plate 14 may communicate with a pattern generator 16 to energize the stimulators to stimulate the brain 18. The pattern generator 16 may generate a regular or random stimulation pattern independent of the environment or other sensory input to, or response by, the patient.

FIG. 2 illustrates an alternative version of the invention wherein the device may provide feedback 19 from a sensor 20, for example, a sensor monitoring a patient activity such as movement of a limb or the like. The sensor 20 may also or alternatively monitor an external event 21 related to the environment and possibly related to patient activity, for example, describing a lever that the patient must grasp. The output of the sensor 20 may be received by a controller 23 that may provide an audio, video or other sensory signal 24 back to the patient, for example, so that the patient might better know the status of his/her performance of the activity. The controller 23 may also synchronize the pattern generator 16 with the external signal 21 or feedback signal 19 as indicated by process block 25 so that the stimulation may be linked to particular activities by the patient or stimuli from the external environment, for example, if it appears that the patient's performance is substandard. The patient activity generating the feedback signal 19 and the external signal 21 is preferably related to the neural pathways to be rehabilitated. For example, the feedback signal 19 may measure a muscular tremor related to impairment such as Parkinson's disease, multiple sclerosis, autism, Alzheimer's disease, vertigo, depression, or insomnia. It is believed that this non-invasive neuromodulation 15, together with the sensory signals 24 from the activity itself, primes or up regulates those neurons of the brain 18 associated with the activity 22 and thereby encourages a therapeutic rehabilitation of the affected areas of the brain 18.

FIG. 3 shows another exemplary version of the invention wherein the stimulation of the non-invasive neuromodulation 15 is independent from and unsynchronized with the sensory signals 24 produced by the activity 30, although it occurs contemporaneously with the activity 30. In this case the sensor 20 might, for example, be a finger cuff bearing accelerometers whose output is processed by a controller to provide sensory signals 24 (here a trajectory display on a terminal 25). At the same time, stimulation may be driven by the pattern generator 16 independently from the sensory signals 24. As noted previously, the therapeutic effects provided by the non-invasive neuromodulation 15 tend to continue after the non-invasive neuromodulation 15 ceases.

As previously noted, the pulses delivered by the stimulators can be random or repeating. The location of pulses can be varied across the stimulator array such that different stimulators are active at different times, and the duration and/or intensity of pulses may vary from stimulator to stimulator. It is believed that the nature of the pulses is not as important as the simple fact that the pulses are delivered during a task for which the patient wishes to improve his/her performance. The pulses therefore need not be delivered in dependence on any factors occurring outside the device during delivery of the electrical pulses, i.e., the pulses need not be delivered or varied in response to the quality of the patient's performance of the task. However, if desired, the pattern generator might receive feedback from the patient and/or the patient's environment, and might somehow modify pulse delivery in response. For example, more stimulation (e.g., pulse frequency and/or intensity) might be provided if it is detected that the patient's performance of the task is suffering rather than improving.

In practice, stimulation which delivers repeating pulses in the nature of a simple waveform, e.g., a square wave or series of regularly-spaced pulses, has been found to be effective. Also preferred are "bursts" of pulses which repeat at some frequency, with the pulses within the bursts repeating at a higher frequency (for example, as if the peaks or "on" periods of a square wave or other waveform were themselves formed of a series of pulses). The fundamental or harmonic frequency underlying the stimulation waveform may be chosen in dependence on the particular application. As examples, testing and/or inference suggest that the appropriate frequency for sensory dysfunction might be around 40 Hz; for Parkinson's disease, around 30-50 Hz; for involuntary movement/tremor, around 1-40 Hz; for voluntary movement coordination, around 50-100 Hz; for cognitive processes, around 100-300 Hz; for bradykinesia, around 150 Hz; for sleep or anesthesia, around 80 Hz; and for relaxation or wakefulness, around 0.5-2.0 Hz. In some applications, it may be most effective to have the delivery frequencies of certain electrodes (or other actuators/elements for delivering stimulation) differ in accordance with their location, e.g., electrodes in one area may deliver stimulation at one frequency and electrodes at another area deliver stimulation at another frequency (wherein the frequencies need not necessarily have a harmonic relationship).

As also previously noted, stimulation may be provided by electrical, mechanical, thermal, or electromagnetic actuators/elements, which may vary in their sizes and geometric configurations. Electrodes used in testing have typically been circular electrodes measuring between 1-10 mm in diameter, but electrodes may be differently sized and configured as desired. Cutaneous electrical stimulation of cranial nerve branches has been efficiently and inexpensively delivered using surface electrodes held gently against the skin or oral tissue using masks (including full or partial facial masks, e.g., patches or frameworks covering a portion of the face) and collars (including both neck collars and bands/sleeves fitting about portions of the head) which preferably situate the electrodes thereon to at least partially conform to the contours of the skin surface over which they are placed. The electrode material may be chosen to minimize corrosion and skin irritation, with possible electrode materials including gold, titanium, platinum, rhodium, and/or stainless steel. The electrode surface material may be full-thickness or a thin layer deposited by electroplating, vapor deposition, ion implantation, or similar processes. The electrode may be conductive, or possibly insulating so that only a capacitive displacement current flows into the skin. Insulating materials include various oxides of silicon, titanium, strontium, and/or tin, as well as various polymers such as polyester, polyimide, and/or polyamide-imide. Both mechanical and electrical contact between the electrode and skin may be further enhanced by the use of electrically conductive materials such as electrode gels (with or without conductive electrolytes) or distensible conductive polymers. Both gels and polymers may additionally have adhesive properties to further improve the electrode-skin interface. Exemplary materials of this nature are presently in common use for biopotential recording electrodes (e.g., for electrocardiography and electroencephalography), as well as for electrodes used for functional electrical stimulation (e.g. for neuromuscular stimulation or transcutaneous electric nerve stimulation for pain relief).

Where electrodes are used to deliver electrical stimulation, the pulses may be generated by oscillator/pulse generator circuits which deliver the desired frequency, voltage, current, power, or other electrical pulse property to the electrode-skin interface. Skin stimulation generally involves voltages of 10-500 volts and currents of 0.5-50 milliamps depending on factors such as electrode geometry and the location and condition of the site at which the electrode is to be placed. For oral tissue stimulation, similar currents but lower voltages of 1-40 volts may suffice. As previously noted, the stimulus waveform may have a variety of time-dependent forms, and for cutaneous electrical stimulation, pulse trains and bursts of pulses have been found useful. Where continuously supplied, pulses may be 1-500 microseconds long and repeat at rates from 1-1000 pulses/second. Where supplied in bursts, pulses may be grouped into bursts of 1-100 pulses/burst, with a burst rate of 1-100 bursts/second. A particularly effective cutaneous stimulus uses 25-50 microsecond pulses repeating at a rate of 200 pulses/second, with every fourth pulse omitted to yield a 3 pulse/burst structure that repeats at 50 bursts/second.

As briefly discussed earlier, mechanical stimulation (if used) may be delivered by various kinds of devices such as electromagnetic solenoids, shape-memory alloy (e.g. tin-nickel) actuators, piezoelectric actuators, electrically-active polymer actuators, electrorheological actuators, motors, electrostatic actuators, pneumatic or hydraulic cylinders or other devices, and micromechanical systems (MEMS) devices. The stimulation devices may be held against the skin by masks, collars, and other devices as described above for use with electrodes. Preferably, a mechanical actuator would be limited in size to agitate an area ranging between perhaps 1 square millimeter to 1 square centimeter of skin per actuator, but the size of the actuator (and thus the affected area) may be larger or smaller as necessary; for example, it is possible to construct a mechanical actuator that provides mechanical stimulation to an entire large skin area (e.g., the entire face) at once, as by using a vibrating rigid mask. The time dependency of mechanical stimulation is typically sinusoidal, with a rate of 1-1000 Hz and a displacement of 0.1 micrometer to 5 millimeters, but different stimulation waveforms/patterns may be used instead. A variation on mechanical stimulation is the use of high-frequency (0.1-10 megahertz) ultrasonic stimulation which may be modulated to produce a varying "wave pressure" mechanical stimulation of subcutaneous nervous system tissue.

It is believed that stimulation of the trigeminal nerve (the fifth cranial nerve or CN-V) or branches thereof provides particularly rapid and potent rehabilitative effect, though it is possible that stimulation of parts of the body other than the head and neck—and thus nerves other than the trigeminal nerve—might work suitably well. Stimulation of the tongue affects the lingual nerve, a branch of the mandibular nerve (CN-V3), one of the three major divisions of the trigeminal nerve. Cutaneosensory information delivered to the lower lip, chin, jaw, and lower cheek up to the sides of the scalp also affects the mandibular nerve. Another major division of the trigeminal nerve, the maxillary nerve (CN-V2), receives cutaneosensory information from the region of the upper lip, lateral aspect of the nose, upper cheeks, below the eyes, and the temples. The final division of the trigeminal nerve, the opthalmic nerve (CN-V1), receives cutaneosensory information from the upper anterior two-thirds of the upper scalp, and the anterior third of the face that includes the forehead, nose, and regions above the eyes.

Stimulation of the facial nerve (CN-VII) or branches thereof is also believed to be particularly beneficial, in part because such stimulation may provide antidromic (backward) stimulation of the facial nerve nucleus of the brainstem. Stimulation of the facial nerve can perhaps be most easily effected via stimulation of the oral cavity; for example, when stimulation is provided to the tongue via a mouthpiece, the facial nerve is effectively stimulated via the chorda tympani (taste nerve), a branch of the facial nerve. However, stimulation of other branches of the facial nerve might also be effected by use of one or more stimulators situated on masks, collars, or other devices which fit over all or a portion of the face, or other areas of the head and/or neck.

Other regions for which stimulation may be particularly effective include the back of the head, the dorsal part of the neck, and the middle of the shoulders. Stimulating these areas affects afferent nerves of the medial branches of the dorsal rami of the cervical spinal nerves (greater occipital-c2, occipital-c3, and c4-7, respectively). The areas above and behind the ear (lesser occipital-c2,3), below the ear (greater auricular-also c2,3), the anterior neck (transverse cervical-also c2,3), and beneath the jaw and chin (supraclavicular-c3,4) can also be useful.

A preferred methodology for therapeutically administering the invention is briefly described above, and is now discussed in greater detail. It should be understood that this methodology is merely one which has proven effective in preliminary testing, and that variations from this methodology are possible, and are regarded as being encompassed by the invention. The following steps of the methodology are preferably performed in the order presented below.

Initially, the patient is preferably queried to assess current health and functional state (emotional, physical and cognitive). This may include an oral interview and/or testing, and known and conventional interviews/tests such as the Short Form-36 (SF-36, for general evaluation of physical and mental health), the Continuous Cognitive Performance Test (for measuring cognition/attention), the Hamilton Depression Scale (HAM-D, for measuring depression severity), the Dynamic Gait Index (for measuring gait and the likelihood of falling), the Dizziness Handicap Index (DHI, for measuring the severity of vestibular disorders), the Activities-specific Balance Confidence Scale (ABC, for measuring fear of falling), the Multiple Sclerosis Impact Scale (MSIS, for measuring the severity of symptoms of multiple sclerosis), and/or other tools may be employed.

The patient may then be educated about the global, daily, and session-specific objectives of the therapy. This may include familiarization with the stimulation routine, hardware, and software to be used in the therapy. This can help to alleviate patient anxiety, and increase cooperation and confidence.

The patient is then preferably physically conditioned within the limits of the patient's (initial) ability, without any stimulation being applied, wherein the conditioning at least partially encompasses actions which are hindered by the patient's functional deficit. This can be useful to familiarize the patient with the planned therapy for the day; to redevelop body awareness of potential ability and of unconscious adaptations the patient may have made; and to give the therapist an estimation of the patient's degree of (and confidence in their) brain-body integration.

The patient may then be made to engage in a short (e.g., 5-minute) therapy period wherein the patient performs one or more tasks selected to address the patient's functional deficit (i.e., tasks which are hindered by the patient's functional deficit), with the tasks being performed at a low intensity level while the patient simultaneously receives stimulation. The task intensity is set at a low level to better familiarize the patient with the routine they will be experiencing during the remainder of the therapy session. This step helps build familiarity with a task, and establishes confidence in task performance. This step may be followed by a short (e.g., 3-minute) rest period.

The patient then preferably engages in a short (e.g., 5-minute) therapy period wherein the patient performs the same task while receiving stimulation, with the task being modified to present a challenge that is slightly beyond the patient's current functional capacity. The high-intensity challenge may require active reinforcement and redirection by the therapist to ensure the patient performs the task correctly under new operating conditions, and that the patient does not (for example) rely on compensatory strategies that the patient established in response to the functional deficit. This step may be followed by a short (e.g., 3-minute) rest period.

The patient can then engage in a short (e.g., 5-minute) therapy period wherein the patient again performs the same task while receiving stimulation, with the task now being modified to present a moderate challenge that is within the patient's current functional capacity. This familiarizes the patient with the moderate-intensity task. This step may be followed by a short (e.g., 3-minute) rest period.

The patient then preferably engages in a longer therapy period (e.g., 20 minutes) at the same moderate level, with the patient simultaneously receiving stimulation. This period allows for a longer period during which neural plasticity and rehabilitation is induced in the neural structures involved in performing the particular task.

Optionally, stimulation might then be applied (or continued) for a brief period of time while the patient is not engaged in the task. This may be useful to continue stimulation of the neural structures involved in performing the particular task (though other neural structures may be stimulated as well), and may help to enhance rehabilitation.

The patient may then engage in simplified post-therapy querying and assessment using metrics which are the same as or similar to those noted above. This helps to quantify changes in functional capacity, and to assess the need for changes in the rate and type of therapy progression. No stimulation need be applied during this step.

These steps are preferably performed by a patient at least twice per day, with a period of at least 4 hours separating each session (i.e., each set of steps). If more than one session is performed per day, some of the steps (e.g., the first and second steps) might be omitted for the sessions following the first one.

It is believed that the benefits of the invention are not limited to neurorehabilitation to at least partially restore impaired movement or physical function, and that the benefits extend to other human capabilities that depend on neurological function. In particular, it is believed that the benefits of the invention extend to at least partial restoration of mental capabilities as well as physical capabilities. For example, rehabilitation of impaired cognitive (e.g. attention, memory, learning, multitasking, etc.) function may be improved by providing stimulation during tasks designed to exercise perceptual and cognitive skills. Such tasks could include commonly available "brain-training" exercises or games, e.g., computerized or non-computerized exercises or games designed to require use of attention span, memory/recollection, reading comprehension, etc. For example, a patient with memory impairment due to Alzheimer's disease might perform a set of memory exercises of progressively greater difficulty in conjunction with stimulation, thereby functionally and structurally improving memory circuitries via induced synaptic plasticity. Beneficially, mental exercises of this nature can be readily delivered to a patient via computer (as in the nature of tests, puzzles, or other queries directed to the patient via a computer screen or other output device), with the computer collecting the patient's responses, thereby reducing the need for (and expense of) therapist involvement. Because the benefits of stimulation are not specific to any particular disease mechanism, they may be beneficial for a wide range of degenerative, traumatic, or degenerative causes of cognitive impairment, including (but not limited to) Parkinson's disease, multiple sclerosis, stroke, head trauma, autism and cerebral palsy.

As another example, it is believed that the invention can provide benefits for at least some type of mood disorders, e.g. depression, anxiety, bipolar disorder, schizophrenia, post-traumatic stress disorder, obsessive-compulsive disorder, etc. In these cases, the tasks performed by the patient might include those that are commonly used during therapies for mood disorders, e.g. cognitive-behavioral therapy exercises, progressive exposure to "triggers" for compulsive behaviors, visualization exercises, meditation, relaxation techniques, etc. Here too stimulation may enhance functional and structural plastic changes associated with the therapeutic task, causing the new behaviors practiced during the therapy to become more automatic.

It is further believed that the invention can also assist in the enhancement of nonimpaired physical and/or mental capabilities, as well as assisting in at least partial restoration of impaired physical and/or mental capabilities. Thus, the invention might assist with proficiency in physical and/or mental activities such as sports activities, reading/studying, playing of a musical instrument, etc. in "patients" who do not have any recognized impairment in these fields. As for patients having impaired neurological states, the combination of stimulation and practicing the particular task (physical, cognitive or psychological) will enhance the plastic learning response of the areas and systems of the brain engaged in performance of that task.

It is also emphasized that the application of stimulation is believed to be beneficial where the stimulation is applied prior to and/or after performance of tasks, as well as during performance of such tasks. Application of stimulation before, during, and/or after any task will potentially enhance the efficiency (and efficacy) of neural circuitries responsible for performance of that task, by changing the neuro-chemical environment, the physical structure, and/or other physiological aspects of these neural circuitries. For example, stimulation before the task may create chemical changes that prime the neural tissue to be more receptive to plastic changes; stimulation during the task may increase the baseline neural activity to enhance the plastic response to task performance; and stimulation after the task may enhance consolidation of structural and functional changes related to the task.

It should be understood that the versions of the invention described above are merely exemplary, and the invention is not intended to be limited to these versions. Rather, the scope of rights to the invention is limited only by the claims set out below, and the invention encompasses all different versions that fall literally or equivalently within the scope of these claims.

The invention claimed is:

1. A method of providing non-invasive neurostimulation to enhance a subject's proficiency in an exercise, the method comprising:
    (a) engaging a subject in a physical or mental exercise in which the subject does not have a physical, cognitive, or emotional impairment;
    (b) providing intraoral cutaneous stimulation of at least one of the subject's trigeminal nerve or facial nerve, or indirectly effecting neuromodulation in the subject's hypoglossal nerve nuclei, by delivering electrical pulses to one or more stimulators situated within the subject's oral cavity, the delivery of electrical pulses being (i) contemporaneous with and independent of the subject's engagement in the exercise, and (ii) independent of the subject's surrounding environment; and
    (c) repeating steps (a) and (b) on a periodic basis.

2. The method of claim 1 wherein step (a) further comprises engaging the subject in one or more of a sports activity, reading, eye and movement exercises, studying, voice and swallowing training, playing a musical instrument, operating a vehicle, sleep or relaxation.

3. The method of claim 1 wherein step (a) further comprises engaging the subject in one or more of the following: a brain training exercise, a computerized brain training exercise, a memory recollection exercise, an attention span increasing exercise, or a reading comprehension exercise.

4. The method of claim 1 wherein step (b) further comprises providing stimulation during one or more of a period shortly or immediately before the subject has engaged in the exercise, or a period shortly or immediately after the subject engaged in the exercise.

5. The method of claim 1 wherein step (b) further comprises providing stimulation that is synchronized with the subject's engagement in the exercise.

6. The method of claim 1 wherein step (b) further comprises providing stimulation by delivering electrical pulses to the at least one electrode in a random or repeating pattern that is independent of events occurring outside the signal generator.

7. The method of claim 1 wherein step (b) further comprises delivering electrical pulses to one or more electrodes of an electrode array.

8. A method of providing non-invasive neurostimulation to enhance a subject's proficiency in a cognitive exercise, the method comprising:
(a) engaging a subject in a cognitive exercise in which the subject does not have an impairment;
(b) providing, by a signal generator, stimulation of at least one of the subject's trigeminal nerve or facial nerve, or indirectly effecting neuromodulation in the subject's hypoglossal nerve nuclei, by delivering electrical pulses generated by the signal generator to the subject's oral cavity via at least one electrode in contact with the subject's oral cavity, the delivery of electrical pulses being (i) contemporaneous with and independent of the subject's engagement in the cognitive exercise, and (ii) independent of the subject's surrounding environment; and
(c) repeating steps (a) and (b) on a periodic basis.

9. The method of claim 8 wherein the stimulation is generated by a signal generator.

10. The method of claim 8 wherein step (a) further comprises engaging the subject in one or more of a sports activity, reading, eye and movement exercises, studying, voice and swallowing training, playing a musical instrument, sleep or relaxation.

11. A method of providing non-invasive neurostimulation to enhance a subject's proficiency in a physical exercise comprising:
(a) engaging a subject in a physical exercise in which the subject does not have an impairment;
(b) providing, by a signal generator, stimulation of at least one of the subject's trigeminal nerve or facial nerve, or indirectly effecting neuromodulation in the subject's hypoglossal nerve nuclei, by delivering electrical pulses generated by the signal generator to the subject's oral cavity via at least one electrode in contact with the subject's oral cavity, the delivery of electrical pulses being (i) contemporaneous with and independent of the subject's engagement in the physical exercise, and (ii) independent of the subject's surrounding environment; and
(c) repeating steps (a) and (b) on a periodic basis.

12. The method of claim 11 wherein the electrical pulses are generated by a signal generator.

13. The method of claim 11 wherein the physical exercise includes one or more of a sports activity, reading, studying, playing a musical instrument, operating a vehicle, sleep or relaxation.

14. The method of claim 11 wherein the stimulation occurs during one or more of a period shortly or immediately before the subject has engaged in the exercise, or a period shortly or immediately after the subject engaged in the exercise.

15. The method of claim 11 wherein the stimulation is unsynchronized with the subject's engagement in the exercise.

16. The method of claim 11 wherein the stimulation includes electrical pulses delivered to the one or more stimulators in a random or repeating pattern that is independent of the subject's engagement in the exercise or uses a close-loop model based on neurofeedback from the subject.

17. The method of claim 11 wherein the physical exercise includes (i) performing the exercise at high intensity; and (ii) subsequently performing the exercise at moderate intensity.

18. The method of claim 17 wherein the physical exercise includes performing the exercise at low intensity before performing the exercise at high intensity.

19. The method of claim 11 wherein the stimulation includes delivering electrical pulses to one or more electrodes of an electrode array.

* * * * *